United States Patent [19]

Arwidsson et al.

[11] Patent Number: 5,783,215
[45] Date of Patent: Jul. 21, 1998

[54] PHARMACEUTICAL PREPARATION

[75] Inventors: Hans Arwidsson, Mariefred; Lars Stubberud, Södertälje, both of Sweden

[73] Assignee: Astra Aktiebolag, Sodertalie, Sweden

[21] Appl. No.: 464,773

[22] PCT Filed: Jun. 7, 1995

[86] PCT No.: PCT/SE95/00676

§ 371 Date: Jun. 22, 1995

§ 102(e) Date: Jun. 22, 1995

[87] PCT Pub. No.: WO96/01621

PCT Pub. Date: Jan. 25, 1996

[30] Foreign Application Priority Data

Jul. 8, 1994 [SE] Sweden ................... 9402422

[51] Int. Cl.⁶ ............... A61K 9/50; A61K 9/58; A61K 9/14; A61K 9/22
[52] U.S. Cl. ............ 424/501; 424/489; 424/493; 424/494; 424/500
[58] Field of Search ................... 424/501, 500, 424/489, 493, 494

[56] References Cited

U.S. PATENT DOCUMENTS 4,713,248  12/1987  Kjørnaes ................... 424/468
5,026,560  6/1991  Makino ................... 424/494

FOREIGN PATENT DOCUMENTS

| | | |
|---|---|---|
| 0277741 | 8/1988 | European Pat. Off. . |
| 0305918 | 3/1989 | European Pat. Off. . |
| 0361874 | 4/1990 | European Pat. Off. . |
| 0277127 | 4/1991 | European Pat. Off. . |
| 0447168 | 9/1991 | European Pat. Off. . |
| 0452862 | 10/1991 | European Pat. Off. . |
| 0475536 | 3/1992 | European Pat. Off. . |
| 0277874 | 4/1993 | European Pat. Off. . |
| 3241889 | 9/1991 | United Kingdom . |
| 8503436 | 8/1985 | WIPO . |

OTHER PUBLICATIONS

Abstract PDD 7397 from AAP's Congress, U.S.A., Pharmaceutical Research (Supplement), 1993.
Drug Development and Industrial Pharmacy, 18(18), 1927–1944 1992.
International Journal of Pharmaceutics, 95 (1993), 29–42.
International Journal of Pharmaceutics, 103 (1994), 55–67.

*Primary Examiner*—Fred Zitomer
*Attorney, Agent, or Firm*—White & Case L.L.P.

[57] ABSTRACT

Controlled release beads containing a core around which is a drug-containing layer e.g. a layer containing furosemid and a process for their preparation and their use in a pharmaceutical preparation. The controlled release beads have excellent mechanical and release characteristics.

22 Claims, No Drawings

PHARMACEUTICAL PREPARATION

FIELD OF THE INVENTION

The present invention relates to controlled release beads and a novel pharmaceutical preparation containing a core around which is a drug-containing layer e.g. a layer containing an active substance. i.e. a practically insoluable active substance, preferably furosemid to the use of said preparation and to a process for preparing the same.

BACKGROUND OF THE INVENTION

The present invention provides a novel a pharmaceutical multiple unit dose preparation with very favourable characteristics which may withstand mechanical stress, i.e. during compaction. These favourable mechanical characteristics are advantageous when dealing with multiple unit dose systems comprising modified or controlled release properties.

A common problem with multiple unit dose systems designated to have modified or controlled release properties is their sensitivity to mechanical stress, e.g. compaction stress, giving rise to rupturing and cracking of the release controlling membrane (Bechard and Leroux 1992) or fragmentation of the core (Magnatiand Celik 1994).

Multiple unit dosage systems may be filled into capsules or sachets, thus requiring sufficient mechanical properties to withstand processing. It may even be advantageous to compact multiple units into tablets, subjecting the systems to significant mechanical stress.

According to the present invention the problem of mechanical suitability mentioned above has been overcome by using inert and non-soluble cores of glass or sand particles or soluble cores such as sugar spheres capable of withstanding mechanical stress, in combination with a plasticizing layer of a hydrophilic polymer containing the active substance, optionally with additional layers of the polymer not containing the active substance, layered between the core and the release controlling membrane.

PRIOR ART

In abstract PDD 7397 from AAPs congress, USA, Pharmaceutical Research (supplement), 1993, it is described that the coating of pellets provides a physical protection of the pellet core which must remain intact and have suitable mechanical properties in order to be resistant to fragmentation during compaction of the tablet. Fragmentation was, however, found to be between 18 and 42% for ethylcellulose pellets.

In Drug Development and Industrial Pharmacy, 18(8), 1927–1944 (1992), films manufactured from an ethyl cellulose pseudolatex dispersion plasticized with 24% DBS, suitable for the controlled release of chlorpheniramine maleate from small pellets with a size of 250–840 mm, are described. These films do not, however, have the appropriate mechanical properties to withstand compaction forces without rupturing, and the controlled release properties of the compacted pellets are thus lost during the process.

In "Compaction studies on pellets", L. Maganti and M. Celik, International Journal of Pharmaceutics, 95 (1993) 29–42, compaction characteristics of pellets, i.e. cores made from microcrystalline cellulose, dicalciumphosphate, lactose and propranolol HCl, are described, and it is concluded that the pellets exhibit elastic deformation and brittle fragmentation, resulting in compacts of lower tensile strength.

In "Compaction studies on pellets", L. Maganti and M. Celik, International Journal of Pharmaceutics, 103 (1994) 55–67, it is described that the addition of a coating material alters the deformation characteristics of uncoated pellets. Further, it is shown that coated pellets lost their sustained release characteristics after compaction.

U.S. Pat. No. 4,713,248 describes a controlled release multiple unit formulation containing an active substance coated with a water based film comprising a homogeneous combination of water-dispersable film forming agent and a polymeric substance which impart compressability to the coating.

EP 361 874 describes a process for the preparation of a core by spraying core granules with a dispersion of a low substituted hydroxypropylcellulose, and if necessary simultaneously applying a dusting powder. The dispersion or the dusting powder can be incorporated with an active ingredient. The granules obtained exhibit increased granule strength and improved disintegration properties.

EP 277 874 and EP 475 536 describe a technique for coating of cores with a spraying powder containing an active drug and low substituted hydroxypropyl cellulose. As described in EP 361 874 the cores have increased hardness and favourable disintegration properties.

EP 277 127 describes controlled release beads coated with a membrane controlling drug release. The pharmaceutical active compound is dissolved in a solvent and applied onto an insoluble core material with a porosity of less than 15%.

There is not described anywhere in the prior art a controlled release multiple unit system or beads comprising a soluble core, alternatively an insoluble core with a porosity of less than 15% layered with a pharmaceutical practically insoluable (USP XXIII) active substance dispersed in or homogeneously mixed with a hydrophilic polymer, thereby exhibiting excellent mechanical properties.

Outline of the invention

We have now surprisingly found that the problem mentioned above can be solved by the new pharmaceutical preparation according to the present invention. The invention provides a novel, controlled release multiple unit dose formulation having clinical and pharmaceutical advantages and with excellent compaction characteristics withstanding alteration of the dissolution profiles, and hence no altering of the bioavailability and clinical effect, during the compaction.

When forming the pharmaceutical preparation according to the invention it has surprisingly been found that the addition of a hydrophilic polymer in a layer together with the active substance in specified ratios and the ratio of active substance to the core being within specified ratios in the beads, gives favourable mechanical properties withstanding cracking, especially of the release controlling membrane, when exposed to mechanical stresses, e.g. during filling in capsules or sachets or during compaction.

The active substance is, according to the invention, dispersed in a solution of the hydrophilic polymer and applied to the core. By using powder layering, i.e. simultaneously spraying an aqeous solution of the hydrophilic polymer and the active substance as a drug powder onto the core, the principle according to the invention may be obtained. A solution of the active substance dissolved in a solvent may also be used, whereby the solution of active substance is applied onto the core. A release controlling membrane is further applied to obtain controlled release properties. This membrane may also contain additional polymers i.e. usable as coating materials for pharmaceutical purposes.

The layering technique according to the invention, gives multiple unit systems which exhibit sufficient plasticity and flexibility to withstand cracking or rupturing of the release controlling membrane during compaction, i.e. no significant changes in the release profile characteristics of compressed coated pellets relative to uncompressed coated pellets are seen. A combination of the polymer layering of the core and a controlled release membrane containing polymeric substances as described above is also favourable to improve the compaction properties of the multiple units.

The preparation consists of a large number of small inert and insoluble particles, cores, which are layered with an active compound e.g., furosemid, dispersed in a hydrophilic polymer.

The cores have a size of 0.1–2 mm, preferably 0.1–0.5 mm, and most preferably 0.1–0.3 mm, and consists of insoluble inert material, i.e. not soluble in water or physiological fluids, such as glass particles or sand (silicon dioxide) or a soluable core such as sugar spheres. The core material used according to the invention may also consist of insoluble inert plastic materials, i.e. spherical or nearly spherical core beads made out of polyvinylchloride, polystyrene or any other pharmaceutical acceptable insoluble synthetical polymeric material made into beads or pellets.

The core material should have a standardized size and shape, preferably spherical, it should have a high enough density to make possible fluidizing processes.

The pharmaceutically active compound is applied onto the core material preferably by spraying in a fluidized bed with wurster or top spray technique from a dispersion of the compound in a polymeric solution. To allow the spraying process from a dispersion of the particles the particle size of the active compound have to be small, normally less than 100 mm, more preferably less than 30 mm.

The active compound thereby forms a compact layer together with the polymer on the insoluble core. Resulting particles i.e. the controlled release beads have a size of 0.2–3.0 mm, more preferably 0.2–1.5 mm, most preferably 0.2–0.9 mm when filled into capsules and 0.3–1.5 mm for tableting.

The hydrophilic polymer gives the beads plastic properties and even act as a binder. Hydrophilic polymers such as polyvinylpyrrolidone, polyalkylene glycol such as polyethylene glycol, gelatine, polyvinyl alcohol, starch and derivatives thereof, cellulose derivatives such as hydroxymethylpropyl- cellulose, hydroxypropylcellulose, carboxymethyl cellulose, methyl cellulose, propyl cellulose, hydroxyethyl cellulose, carboxyethyl cellulose, carboxymethylhydroxyethyl cellulose or any other pharmaceutically acceptable hydrophilic polymer.

The core particles may be coated with the active substance dispersed in the hydrophilic polymers by powder layering technique, i.e. the active substances is applied to the core in dry form as powder. At the same time the polymer is sprayed onto the cores as a solution in such a way that solvent, preferably water, is evaporated, and the polymer is applied to the cores together with the active substance, i.e. forming a homogenous dispersion.

The ratio of active substance to hydrophilic polymer may be from about 10:1 to about 1:2 for tableting, preferably from about 5:1 to about 1:1, most preferably from about 2:1 to about 1:1, and for filling into capsules preferably from about 10:1 to about 5:1.

The ratio of active substance to inert non-soluble core particles may be from about 5:1 to about 1:2, preferably from about 2:1 to about 1:2.

Preferred active substances are furosemid, carbamazepin, ibuprofen, naproxen, probenecid, indometacin, ketoprofen, spironolactone, felodipin, nifedipin, dipyridamole, pindolol, nitrazepam or dextromethorphan, particularly preferred is furosemid.

The method described above can be used for other pharmaceutical substances as well, provided that they can be dispersed in liquid containing a dissolved hydrophilic polymer, water-based solutions of a hydrophilic polymer is especially preferable. It may even be possible to dissolve the active substance in liquid containing the dissolved polymer prior to spraying onto the cores.

The beads are coated with a polymeric membrane modifying and controlling the drug release. The polymeric membrane can release the drug according to various release profiles, e.g. pH dependent, enteric coating, pH independent, with or without lag time. The most important use is pH independent controlled release in the range of pH 1–8. Examples of suitable polymeric materials are ethyl cellulose, hydroxypropylmethyl cellulose, hydroxypropyl cellulose, hydroxypropylmethyl phtalate (e.g. HP 55), cellulose acetate phtalate, cellulose acetate trimellitate, Eudragit®RL, Eudragit®RS. Ethyl cellulose can be used alone or in a combination with e.g. a water soluble polymer such as hydroxypropylmethyl cellulose to adjust the permeability of the coating layer. Even the copolymerisate of acrylic and methacrylic acid esters or other film-formers mentioned herein may be used in combination with a water-soluble polymer. Other pharmaceutically acceptable polymers which could be incorporated in the film layer are polyvinylpyrrolidone, polyalkylene glycols such as polyethylene glycol, and cellulose derivatives such as hydroxypropyl cellulose, carboxymethyl cellulose, methyl cellulose, propyl cellulose, hydroxyethyl cellulose, carboxyethyl cellulose, carboxymethylhydroxyethyl cellulose, hydroxymethylcellulose, carboxymethylethylcellulose, methyl-hydroxypropylcellulose.

Ethyl cellulose is available in grades having different viscosities. Different kinds of viscosity grades are suitable. Even water-based dispersions of ethylcellulose is suitable.

Eudragit® is the trade name for a number of film coating substances on an acrylic resin basis produced by Rohm Pharma. E.g. Eudragit®RL and RS are copolymers synthetized from acrylic and methacrylic acid esters with a low content of quaternary ammonium groups. The molar ratio of these ammonium groups to the remaining neutral (meth) acrylic acid esters is 1:20 for Eudragit®RL and 1:40 for Eudragit®RS resulting in different permeability characteristics. Other variants of Eudragit® that can be used are Eudragit®L, Eudragit®S and Eudragit®E.

Pigments and/or plasticizers may be added to the polymeric solution in order to improve the technical properties of the membrane or modify the release characteristics. Examples of plasticizers that may be used are citrate esters, acetylated monoglycerides, and glycerinetriacetate.

Organic solutions or water-based dispersions of the polymers, as will be appreciated by the man skilled in the art (e.g. Aquacoat®, Surelease®, Eudragit®E 30 D, Eudragit®L 30 D) could be used for obtaining the membrane modifying and controlling the release of the active substance.

By using the pharmaceutical preparation according to the invention several advantages are obtained.

The coated beads or multiple units described above are favourable in obtaining coated beads filled into capsules or sachets. Especially advantageous according to the invention is when the beads are compressed into tablets. By using the pharmaceutical preparation according to the invention it is possible to compress coated beads into tablets without altering the dissolution profile as a consequence of the mechanical stress during the compaction process. A combination of the layering method described herein and the controlled release film formulation described herein, comprising the film former and a polymeric substance is especially favourable to obtain the excellent compaction characteristics without altering the dissolution profiles, and hence the bioavailability and clinical effect, during compaction.

Use of organic solvents give rise to enviromental pollution, danger of explosions and hazard unless costly recycling procedures are used. From an enviromental point of view the invention is especially favourable as it is possible to layer core material with active substances such as furosemid etc., or other water insoluble substances, by using a dispersion of the active compound in an aqeous solution of hydrophilic polymer, thus without using a solution in organic liquids.

By using powder layering, i.e. simultaneously spraying of an aqueous solution of the hydrophilic polymer and the active substance as dry powder onto the core material, similar enviromental advantages are obtained.

A further advantage with the formulation according to the invention is the incorporation of a hydrophilic polymer together with the active pharmaceutical agent. This may give more favourable possibilities to control the dissolution profile of the uncoated and coated beads, for furosemid at pH values lower than about 4.

The preparation according to the invention is particularly advantageous when controlled and constant release of the therapeutical agent is wanted. A method for the controlled release of the therapeutically active substance e.g., furosemid is a further aspect of the invention. Thus giving flexibility and favourable mechanical properties in such a way that cracking or rupturing of the release controlling membrane is avoided.

Pharmaceutical preparations

The formulation above comprising multiple unit dose systems with a release controlling membrane may be prepared by conventional methods such as fluidized beds with top-spray or wurster techniques or powder layering techniques, or any technique well known to one skilled in the art.

When the pellets are compressed into tablets they are blended with conventional excipients to obtain favourable filling, binding, lubrication and disintegration properties. Examples of excipients are microcrystalline cellulose, lactose, spray dried lactose, dicalcium phosphate, pregelatinized starch, starches and derivatives thereof such as sodium starch glycolate, maltodextrine, sorbitol, maltitol, cellulose and derivatives thereof, polyethylene glycol, polyvinyl pyrrolidone, compressable sugar, stearic acid, magnesiumstearat, sodium stearylfumarate, talc, colloidal silicone dioxide or any other conventional excipient usable for tablet preparation as will be clear to anyone skilled in the art.

The excipients, i.e. the fillers and binders, comprising the tablet may be used as direct compression excipients or they may be granulated into granules with favourable compression characteristics. Disintegrats may or may not be added. Lubricants will normally be added. The amount of fillers and binders, eventually granulated into granules, may be in the range from 25 to 75% of the total tablet weight. To obtain even more favourable compression characteristics it should be between 40 and 75% of the total tablet weight.

The pharmaceutical preparations according to the present invention may be administered orally. Substances, such as furosemid, which are excellent as a medicament against cardiovascular diseases such as hypertension, congestive heart failure and oedema, especially for the treatment of hypertension are of special interest. Other active substances could be used, e.g. substances for the treatment of diuretic, antiepileptic, antiinflammatoric, analgetic conditions.

The following examples will describe the invention in more detail.

EXAMPLE 1

Cores:

| | |
|---|---|
| Silicone dioxide (0.1–0.3 mm) | 1000 g |
| Water, purified | 2000 g |
| Furosemid (90% <25 μm) | 1000 g |
| Polyvinyl pyrrolidone, K-30 | 500 g |

Polymeric Layer:

| | |
|---|---|
| Ethylcellulose | 60.3 g |
| Hydroxypropylmethylcellulose | 13.3 g |
| Triethylcitrate | 6.0 g |
| Ethanol | 1446.5 g |

EXAMPLES 2–4

| | |
|---|---|
| Silicone dioxide (0.1–0.3 mm) | 800 g |
| Water, purified | 1480 g |
| Furosemid (90% <10 μm) | 800 g |
| Polyvinyl pyrrolidone, K-30 | 400 g |

Polymeric Layers:

EXAMPLE 2

| | |
|---|---|
| Ethylcellulose | 292 g |
| Hydroxypropylcellulose | 108 g |
| Ethanol | 3500 g |

EXAMPLE 3

| | |
|---|---|
| Ethylcellulose | 266 g |
| Hydroxypropylcellulose | 134 g |
| Ethanol | 3500 g |

EXAMPLE 4

| | |
|---|---|
| Etylcellulose | 240 g |
| Hydroxypropylcellulose | 160 g |
| Ethanol | 3500 g |

In a fluidized bed granulator furosemid dispersed in a solution of polyvinyl pyrrolidone (K-30) in water was sprayed onto the cores of silicone dioxide. 800 g of the beads so formed were covered with the polymeric solution containing ethyl cellulose and hydroxypropylmethylcellulose, and triethylcitrate in Example 1, ethyl cellulose and hydroxypropylcellulose in Example 24, by spraying a solution of the mentioned substances in ethanol.

FORMULATION EXAMPLES 5–7

The pellets formed according to Example 1 were compressed into tablets containing furosemid in an amount of 30–60 mg. The small beads were thus tabletted by mixing with additives containing e.g. microcrystalline cellulose such as Avicel®, which improves the tableting properites and facilitates the disintegration of the tablet to liberate the individual beads.

Composition for one tablet (mg)

EXAMPLE 5

| Coated pellets (Example 1) | 171.8 |
| --- | --- |
| Microcrystalline cellulose (Avicel ® PH 200) | 171.8 |
| Sodium starch glycolate | 13.7 |
| Magnesium stearate | 0.4 |

EXAMPLE 6

| Coated pellets (Example 1) | 171.8 |
| --- | --- |
| Microcrystalline cellulose (Avicel ® PH 102) | 171.8 |
| Sodium stearylfumarate | 0.3 |

EXAMPLE 7

| Coated pellets (Example 1) | 171.8 |
| --- | --- |
| Microcrystalline cellulose (Avicel ® PH 102) | 171.8 |
| Sodium starch glycolate | 13.7 |
| Sodium stearylfumarate | 0.3 |

The multiple unit pellets described in Example 1 were mixed with equal amounts of microcrystalline cellulose, and further mixed with 4% sodium starch glycolate (example 5 and example 7). Magnesium stearate (example 5) or sodium stearylfumarate (example 6 and example 7) was admixed, and the mixtures were compressed into tablets in a singel punch tablet press at a compression pressure of 8 kN(±1 kN) and 4 kN(±1 kN) at a compression speed of 35 rpm. Flat faced punch with a diameter of 1.13 cm was used. Characterization of the tablets according to example 5

The tablets disintegrated into multiple unit pellets within 30 seconds in 1000 ml purified water at 37° C.

The in vitro dissolution, in accordance with USP Paddle method, 1000 ml buffer pH 6.8, of the tablets compressed at 8 kN, containing 60 mg furosemid, is shown in Table 1.

Reference 1

Cores:

| Silicone dioxide (0.15–0.25 mm) | 1000 g |
| --- | --- |
| Water, purified | 1950 g |
| Furosemid (90% <25 μm) | 1000 g |
| Polyvinyl pyrrolidone, K-90 | 50 g |

Polymeric Layer:

| Ethylcellulose dispersion, 30% (Aquacoat ®) | 170 g |
| --- | --- |
| Acetyltributyl citrate | 13 g |

In a fluidized bed granulator furosemid dispersed in a solution of polyvinyl pyrrolidone (K-90) in water was sprayed onto the cores of silicone dioxide. 800 g of the beads so formed were coated with the aqueous polymeric ethylcellulose dispersion, (Aquacoat®) containing additional plasticizer acetyltributyl citrate. After the coating procedure the coated pellets were heated for 17 hours at 70° C.

The beads described were further, as described in example 5, mixed with equal amounts of microcrystalline cellulose, and further mixed with 4% sodium starch glycolate and 0.1% magnesium stearate and compressed into tablets in a singel punch tablet press at a compression pressure of 8 kN (±1 kN) at a compression speed of 35 rpm. Flat faced punch with a diameter of 1.13 cm was used. The tablets contained 60 mg furosemid.

Table 1 illustrates the release pattern in vitro for ethylcellulose coated beads.

TABLE 1

Dissolution of furosemid from furosemid tablets, 60 mg, prepared according to example 5 and reference 1.
Percentage furosemid released at pH 6.8 (n = 3) after:

|  | 0.5h | 1h | 2h | 3h | 5h | 10h |
| --- | --- | --- | --- | --- | --- | --- |
| Example 5 | 18% | 33% | 52% | 65% | 79% | >90% |
| Reference 1 | 41% | 60% | >80% |  |  |  |

(n = 2)

As is shown in table 1 the pellets when compressed into tablets according to example 5, showed sustained or extended release, properties even when compressed into tablets, whereas pellets prepared according to reference 1 released furosemid relatively fast. The amount of ethylcellulose and plasticizer in relation to pellets was 8% by weight in example 5 and reference 1.

EXAMPLE 8

The pellets formed according to Example 1 were filled into hard gelatine capsules.

EXAMPLE 9 AND 10

Cores:

| Silicone dioxide (0.1–0.3 mm) | 1000 g |
| --- | --- |
| Water, purified | 1900 g |
| Furosemid (90% <25 μm) | 1000 g |
| Polyvinyl pyrrolidone, K-90 | 100 g |

Polymeric Layer:

EXAMPLE 9

| Ethylcellulose dispersion, 30% (Aquacoat) | 128 g |
| --- | --- |
| Acetyltributyl citrate | 10 g |

EXAMPLE 10

| Ethylcellulose dispersion, 30% (Aquacoat) | 170 g |
| --- | --- |
| Acetyltributyl citrate | 13 g |

In a fluidized bed granulator furosemid dispersed in a solution of polyvinyl pyrrolidone (K-90) in water was sprayed onto the cores of silicone dioxide. 800 g of the beads so formed were coated with the aqueous polymeric ethylcellulose dispersion, (Aquacoat) containing additional plastizer acetyltributyl citrate. After the coating procedure the coated pellets were heated for 17 hours at 70° C.

The pellets were finally filled into hard gelatine capsules. Each capsule contained 60 mg furosemid.

The in vitro dissolution of the capsules in accordance with USP Paddle method, 1000 ml buffer pH 6.8, is shown in Table 2.

TABLE 2

Dissolution of furosemid from furosemid capsules, 60 mg, prepared according to examples 9 and 10.
Percentage furosemid released at pH 6.8 (n = 6) after:

|  | 0.5h | 1h | 2h | 3h | 5h | 10h | 13.3h |
|---|---|---|---|---|---|---|---|
| Example 9 | 31% | 48% | 67% | 75% | >90% | — | — |
| Example 10 | 10% | 19% | 33% | 44% | 60% | 70% | >80% |

Formulation Examples 11–24

The pellets formed according to the above given examples 2–4 were compressed into tablets containing furosemid in an amount of 60 mg.
Compositions for one tablet (mg)

EXAMPLE 11

| | |
|---|---|
| Coated pellets (example 2) | 221 |
| Microcrystalline cellulose (Avicel sp. coarse grade) | 331 |
| Sodium starch glycolate | 22 |
| Magnesium stearate | 0.28 |

EXAMPLE 12

| | |
|---|---|
| Coated pellets (example 2) | 221 |
| Microcrystalline cellulose (Avicel PH 302) | 331 |
| Sodium starch glycolate | 22 |
| Magnesium stearate | 0.28 |

EXAMPLE 13

| | |
|---|---|
| Coated pellets (example 2) | 221 |
| Microcrystalline cellulose (Avicel sp. coarse grade) | 331 |
| Sodium stearylfumarate | 0.20 |

EXAMPLE 14

| | |
|---|---|
| Coated pellets (example 2) | 221 |
| Microcrystalline cellulose (Avicel sp. coarse grade) | 331 |
| Crospovidone | 22 |
| Sodium stearylfumarate | 0.20 |

The multiple unit pellets described in example 2 were mixed with 60% microcrystalline cellulose, and further mixed with 4% sodium starch glycolate (example 11 and 12) or Crospovidone (example 14). Magnesium stearate (example 11 and 12) or sodium stearylfumarate (examples 13 and 14) was admixed and, the mixtures were compressed into tablets in a single punch tablet press at a compression pressure of 8 kN (+/−0.4 kN) at a compression speed of 30 rpm. Flat faced punches with a diameter of 1.13 cm were used.

EXAMPLE 15

| | |
|---|---|
| Coated pellets (example 3) | 221 mg |
| Microcrystalline cellulose (Avicel sp. coarse grade) | 221 mg |
| Sodium starch glycolate | 18 mg |
| Magnesium stearate | 0.22 mg |

EXAMPLE 16

| | |
|---|---|
| Coated pellets (example 3) | 221 mg |
| Microcrystalline cellulose (Avicel PH 302) | 221 mg |
| Sodium starch glycolate | 18 mg |
| Magnesium stearate | 0.22 mg |

EXAMPLE 17

| | |
|---|---|
| Coated pellets (example 3) | 221 mg |
| Microcrystalline cellulose (Avicel sp. coarse grade) | 331 mg |
| Magnesium stearate | 0.28 mg |
| Sodium starch glycolate | 22 mg |

EXAMPLE 18

| | |
|---|---|
| Coated pellets (example 3) | 221 mg |
| Microcrystalline cellulose (Avicel sp. coarse grade) | 221 mg |
| Sodium stearylfumarate | 0.18 mg |

EXAMPLE 19

| | |
|---|---|
| Coated pellets (example 3) | 221 mg |
| Microcrystalline cellulose (Avicel sp. coarse grade) | 221 mg |
| Crospovidone | 18 mg |
| Sodium stearylfumarate | 0.18 mg |

The multiple unit pellets described in example 3 were mixed with 50 or 60% microcrystalline cellulose, and further mixed with 4% sodium starch glycolate (example 15–17) or Crospovidone (example 19). Magnesium stearate (example 15–17) or sodium stearylfumarate (example 18 and 19) was admixed and, the mixtures were compressed into tablets in a single punch tablet press at a compression pressure of 12 kN (+/−0.6 kN) and 16 kN (+/−0.8 kN) at a compression speed of 30 rpm. Flat faced punches with a diameter of 1.13 cm were used.

EXAMPLE 20

| | |
|---|---|
| Coated pellets (example 4) | 223 mg |
| Microcrystalline cellulose (Avicel sp. coarse grade) | 334 mg |
| Sodium starch glycolate | 22 mg |
| Magnesium stearate | 0.28 mg |

EXAMPLE 21

| | |
|---|---|
| Coated pellets (example 4) | 223 mg |
| Microcrystalline cellulose (Avicel PH 302) | 334 mg |
| Sodium starch glycolate | 22 mg |
| Magnesium stearate | 0.28 mg |

EXAMPLE 22

| | |
|---|---|
| Coated pellets (example 4) | 223 mg |
| Microcrystalline cellulose (Avicel sp. coarse grade) | 334 mg |
| Sodium stearylfumarate | 0.20 mg |

EXAMPLE 23

| | |
|---|---|
| Coated pellets (example 4) | 223 mg |
| Microcrystalline cellulose (Avicel sp. coarse grade) | 334 mg |
| Crospovidone | 22 mg |
| Sodium stearylfumarate | 0.28 mg |

The multiple unit pellets described in example 4 were mixed with 60% microcrystalline cellulose, and further mixed with 4% sodium starch glycolate (example 20 and 21) or Crospovidone (example 23). Magnesium stearate (example 20 and 21) or sodium stearylfumarate (example 22 and 23) was admixed, and the mixtures were compressed into tablets in a single punch tablet press at a compression pressure of 8 kN (+/−0.4 kN) and 16 kN (+/−0.8 kN) at a compression speed of 30 rpm. Flat faced punches with a diameter of 1.13 cm were used.

Characterization of the tablets formed according to formulation examples 11–21

The tablets disintergrated into multiple unit pellets within 3 minutes in 1000 ml purified water at 37° C.

The in vitro dissolution, in accordance with USP Paddle method, 1000 ml buffer pH 6.8, of the tablets compressed at 8, 12 and 16 kN, containing 60 mg furosemid, is shown in Table 3.

Polymeric layer:

| | |
|---|---|
| Ethylcellulose | 266 g |
| Hydroxypropylcellulose | 134 g |
| Ethanol | 3500 g |

Composition of one tablet (mg)

| | |
|---|---|
| Coated pellets (example 24) | 247 |
| Microcrystalline cellulose (Avicel sp. coarse grade) | 370 |
| Sodium starch glycolate | 25 |
| Magnesium stearate | 0.31 |

The multiple unit pellets described in example 24 were mixed with 60% microscrystalline cellulose, and further mixed with 4% sodium starch glycolate. Magnesium stearate was admixed and, the mixture was compressed into tablets in a single punch tablet press at a compression pressure of 8 kN (+/−0.4 kN) at a compression speed of 30 rpm. Flat faced punches with a diameter of 1.13 cm were used.

The in vitro dissolution, in accordance with USP paddle method, 1000 ml buffer pH 7.4, of the tablets compressed at 8 kN, containing 60 mg Naproxen, is shown in Table 4.

TABLE 3

Percentage furosemide at pH 6.8 (n = 3)

| Examples | Compaction Pressure (kN) | \multicolumn{8}{c}{Percent furosemide dissolved at pH 6.8} |
|---|---|---|---|---|---|---|---|---|---|

| Examples | Compaction Pressure (kN) | 30 | 60 | 120 | 180 (min) | 300 | 600 | 840 | 1200 |
|---|---|---|---|---|---|---|---|---|---|
| 2 | — | 1 | 2 | 4 | 8 | 19 | 56 | 80 | 96 |
| 11 | 8 | 1 | 2 | 5 | 10 | 24 | 69 | 91 | 100 |
| 12 | 8 | 1 | 2 | 5 | 9 | 23 | 67 | 90 | 98.4 |
| 3 | — | 13 | 22 | 56 | 88 | 100 | | | |
| 15 | 12 | 12 | 21 | 50 | 82 | 100 | | | |
| 16 | 12 | 9 | 18 | 46 | 79 | 100 | | | |
| 17 | 16 | 8 | 17 | 49 | 84 | 100 | | | |
| 4 | — | 14 | 34 | 83 | 100 | | | | |
| 20 | 8 | 11 | 36 | 90 | 100 | | | | |
| 20 | 16 | 12 | 39 | 97 | 100 | | | | |
| 21 | 8 | 11 | 38 | 98 | 100 | | | | |

EXAMPLE 24

| | |
|---|---|
| Silicone dioxide (0.1–0.3 mm) | 800 g |
| Water, purified | 1480 g |
| Naproxen | 800 g |
| Polyvinyl pyrrolidone, k-30 | 400 g |

TABLE 4

Percentage naproxen at pH 7.4 (n = 3)

| Exampel | Compaction Pressure | \multicolumn{5}{c}{Percent naproxen dissolved at pH 7.4} |
|---|---|---|---|---|---|---|

| Exampel | Compaction Pressure | 30 | 60 | 120 | 180 | 300 |
|---|---|---|---|---|---|---|
| 24 | | | | | | |
| Pellets | — | 10 | 30 | 76 | 96 | 99 |
| Tablets | 8 | 9 | 32 | 79 | 98 | 100 |

Conclusion

By using the principles described herein reproducible and controllable production processes for multiple unit systems compressed into tablets or filled into capsules or sachets are obtained. Further this new formulation principle gives excellent multiple unit systems withstanding mechanical stresses and giving enough flexibility and plasticity to avoid cracking or rupturing of release controlling membranes.

We claim:

1. A controlled release bead or multiple thereof having a size varying between 0.2–3.0 mm, comprising:

(a) a multiple of a core unit of an insoluble or soluble inert material of a size of 0.1–2 mm;

(b) a first layer on the core unit comprising an active ingredient dispersed in a hydrophilic polymer; wherein the ratio of the active ingredient to the hydrophilic polymer is in the range of from about 10:1 to about 1:1, and the ratio of the active ingredient to the inert insoluble or soluble core is in the range of from about 5:1 to about 1:2;

(c) an optional second layer of hydrophilic polymer covering the first layer; and (d) an outermost membrane layer effective for controlled release of the active ingredient;

the bead or multiplicity thereof exhibiting improved mechanical and release properties so as to withstand alteration in terms of bioavailability and clinical efficacy due to compaction into a multiple unit tablet.

2. The controlled release bead or multiple thereof according to claim 1 wherein the ratio of the active ingredient to hydrophilic polymer is in the range of from 5:1 to about 1:1.

3. Controlled release beads according to claim 1, wherein the cores have a size of 0.1–0.3 mm.

4. The controlled release bead or multiple thereof according to claim 3, wherein the core unit comprises as a first layer the active ingredient dispersed in a hydrophilic polymer; and an outer membrane for controlled release.

5. The controlled release bead or multiplicity thereof according to claim 4, wherein the hydrophilic polymer is polyvinyl pyrrolidone.

6. The controlled release bead or multiplicity thereof according to claim 1, wherein the beads have a size of 0.2–1.5 mm.

7. The controlled release bead or multiplicity thereof according to claim 4, wherein the active substance is furosemid.

8. A process for preparation of the controlled release bead or multiple thereof according to claim 1, comprising the steps of:

(a) dispersing the active ingredient having a particle size of less than 100 μm in a solution of a hydrophilic polymer (b) spraying a first layer of the dispersal of active ingredient in hydrophilic polymer onto the insoluble inert core unit or multiple thereof, and (c) spraying the outer membrane for controlled release onto the first layer.

9. A process according to claim 8, wherein the hydrophilic polymer is polyvinyl pyrrolidone.

10. A pharmaceutical preparation comprising controlled release beads according to claim 1, optionally together with pharmaceutically acceptable excipients.

11. A pharmaceutical preparation according to claim 10, wherein the active substance is furosemid.

12. A pharmaceutical preparation according to any one of claims 10 or 11, wherein the amount of active substance is in the range 20–100 mg.

13. A pharmaceutical preparation according to claim 12, wherein the amount of active substance is in the range 30–60 mg.

14. The pharmaceutical preparation according to claim 10, wherein the beads have improved properties so as to resist alterations in terms of bioavailability and clinical efficacy during compaction into tablets.

15. A pharmaceutical preparation according to claim 14, wherein the ratio of active substances to hydrophilic polymer is of from about 5:1 to about 1:1 and the ratio of active substance to inert non-soluble core particles is of from about 2:1 to about 1:2.

16. A pharmaceutical preparation according to claim 15, wherein the ratio of active substance to hydrophilic polymer is of from about 2:1 to about 1:1 and the ratio of active substance to inert non-soluble core particles is of from about 2:1 to about 1:2.

17. A pharmaceutical preparation according to claim 12, in the form of capsules.

18. A pharmaceutical preparation according to claim 17, wherein the ratio of active substance to hydrophilic polymer is of from about 10:1 to about 5:1 and the ratio of active substance to inert non-soluble core particles is of from about 2:1 to about 1:2.

19. A pharmaceutical preparation according to claims 10–18 which is administered orally.

20. A process for the manufacture of a pharmaceutical preparation according to claim 14, wherein the cores are compressed into tablets by mixing with additives.

21. A method for the treatment of hypertension, oedemas and congestive heart failure wherein a pharmaceutical preparation according to claim 10–19 is administered to a host in the need of such treatment.

22. The process according to claim 8, wherein a second layer of the hydrophilic polymer is sprayed onto the first layer before adding the controlled release membrane onto the bead core unit.

* * * * *